(12) United States Patent
Wu et al.

(10) Patent No.: US 11,844,963 B2
(45) Date of Patent: Dec. 19, 2023

(54) SYSTEMS AND METHODS FOR SYNTHETIC PHOTON RADIATION THERAPY

(71) Applicant: Duke University, Durham, NC (US)

(72) Inventors: Qiuwen Wu, Durham, NC (US); Bo Liu, Durham, NC (US); Fugen Zhou, Durham, NC (US); Xile Zhang, Durham, NC (US)

(73) Assignee: Duke University, Durham, NC (US)

( * ) Notice: Subject to any disclaimer, the term of this patent is extended or adjusted under 35 U.S.C. 154(b) by 459 days.

(21) Appl. No.: 16/918,779

(22) Filed: Jul. 1, 2020

(65) Prior Publication Data

US 2021/0001152 A1 Jan. 7, 2021

Related U.S. Application Data

(60) Provisional application No. 62/869,165, filed on Jul. 1, 2019.

(51) Int. Cl.
*A61N 5/10* (2006.01)
*G16H 20/40* (2018.01)
*G01T 1/02* (2006.01)

(52) U.S. Cl.
CPC ......... *A61N 5/1071* (2013.01); *A61N 5/1031* (2013.01); *A61N 5/1047* (2013.01);
(Continued)

(58) Field of Classification Search
CPC ............ A61N 2005/1074; A61N 5/103; A61N 5/1031; A61N 5/1047; A61N 5/1071;
(Continued)

(56) References Cited

U.S. PATENT DOCUMENTS

2002/0168048 A1* 11/2002 Wong ................. A61N 5/10
378/65

OTHER PUBLICATIONS

Zhang, Y., Feng, Y., Ming, X., & Deng, J. (2016). Energy modulated photon radiotherapy: A Monte Carlo Feasibility Study. BioMed Research International, 2016, 1-16. https://doi.org/10.1155/2016/7319843 (Year: 2016).*

(Continued)

*Primary Examiner* — Thaddeus B Cox
*Assistant Examiner* — Marc D. Honrath
(74) *Attorney, Agent, or Firm* — POLSINELLI, PC

(57) ABSTRACT

Example methods and systems for photon energy synthesis and introducing energy modulation into radiation treatment planning process and delivery process are provided. Example methods comprise obtaining, via a linear accelerator, a first photon energy beam dosimetric data, a second photon energy beam dosimetric data, and an intermediate photon energy beam dosimetric data, and fitting the first photon energy beam dosimetric data and the second photon energy beam dosimetric data according to a preset fitting coefficient. A synthesized photon beam is then generated from dosimetric data from the fitted first photon energy beam dosimetric data and the fitted second photon energy beam dosimetric data. Further, continuously variable photon energies can be derived, where two or more existing photon energy beams are combined linearly and applied to both forward and inverse radiation planning modules for a radiation treatment plan.

14 Claims, 12 Drawing Sheets
(6 of 12 Drawing Sheet(s) Filed in Color)

(52) U.S. Cl.
CPC .............. *A61N 5/1077* (2013.01); *G01T 1/02* (2013.01); *G16H 20/40* (2018.01); *A61N 2005/1074* (2013.01)

(58) Field of Classification Search
CPC ...... A61N 5/1075; A61N 5/1077; G01T 1/02; G16H 20/40
See application file for complete search history.

(56) References Cited

OTHER PUBLICATIONS

Tahmasebi Birgani, M. J., Chegeni, & N., Tahmasbi, (2019). Calculating weighting factors for mixing megavoltage photon beams to achieve desirable dose distribution in radiotherapy. Journal of Biomedical Physics and Engineering, 9(3), 279-284. https://doi.org/10.31661/jbpe.v0i0.789 (Year: 2019).*

* cited by examiner

SYSTEMS AND METHODS FOR SYNTHETIC PHOTON RADIATION THERAPY

CROSS-REFERENCE TO RELATED APPLICATIONS

This application claims priority to U.S. Provisional Patent Application No. 62/869,165 filed 1 Jul. 2019, the entirety of which is incorporated herein by reference.

BACKGROUND

Radiation treatments are currently delivered using a medical linear accelerator (Linac), wherein electrons are accelerated in pulses to high energies, typically comprising energy in the range of 4-25 megavolts (MeV). The majority of such treatments are in the photon mode, where the mono-energetic electrons hit a high Z target (such as Tungsten), and produce photons through Bremsstrahlung radiation. The resulting photons have a continuous energy spectrum, with energies ranging from zero to the initial electron beam energy. Thus, as an example, a 6 MeV electron beam can produce a photon beam having energy between 0 and 6 MeV, such a photon beam is also called a 6 MV photon. Photon beams are the dominant modality in radiation therapy because the beams can penetrate a significant depth to reach a tumor.

Photon beam energy is one of the required parameters in a physician written directive for a prescription and for a treatment plan, and is checked as the treatment is devised and delivered to a patient. Currently, because of the complexity of the Linac engineering and the requirement of the dose rate output, the standard design of a given Linac only allows two to three photon energies to be available. Should more photon energies be desired on a single Linac, a significant increase in the cost of engineering and manufacturing would arise. As one example, beam energy matching can be practiced by the Linac vendor at the request of the customer for the convenience of transferring patients between these energy matched Linacs. This is accomplished by tuning the photon beam energy of the Linac so that its radiation characteristics match with those from another Linac with predefined criteria. However, this is usually performed at an additional cost to the customer, and such energy will be programmed into the Linac and cannot be changed later.

During the commissioning of a Linac for use in radiation treatment, various dosimetric quantities such as percent depth dose (PDD), profiles, output factors (OFs), and the like must be measured by qualified medical personnel in water phantom and in air under all possible geometric conditions allowed by the Linac, and they must be entered into the treatment planning system (TPS) individually to generate appropriate dose calculation models before treatment planning can be performed on actual patients.

The choice of photon energy is currently based largely on experience of the operator and the available photon energies on the Linac machine. For shallow depth targets, such as brain tumors and breast cancers, for example, low energy photon beams are prescribed to spare the distal normal and critical organs. For deep seated targets, such as prostate tumors, tumors in the abdomen, and thoracic regions, high energy photon beams are chosen because of their availability to penetrate deeper and spare the surface region. Currently, the operator can only choose from the few, discrete available energy levels available on that specific Linac.

The prevalence of optimization algorithms and faster computers, coupled with further developed knowledge in clinical outcomes, results in the increased practice of precision radiation therapy to maximize the therapeutic ratio, where the radiation treatment problem is formulated using mathematical equations, and sophisticated optimization algorithms can be utilized to solve the equations so that the radiation dose to the target is maximized while minimizing radiations to the nearby critical organs. Typical examples are intensity modulated therapy (IMRT) and volumetric modulated arc therapy (VMAT). IMRT is a precise method of radiation delivery, wherein the shapes and weights of hundreds or thousands of sub-fields from the same direction are individually tuned to conform the radiation dose to the target and avoid the surrounding critical structures. VMAT is another precise method of radiation delivery wherein the shapes and weights of hundreds of sub-fields from different directions as the treatment machine rotates around the patient are individually tuned to accurately shape the radiation dose to the tumor while avoiding or minimizing the exposure of the surrounding critical structures.

However, energy modulation, that is, the ability to continuously vary the energy during the radiation treatment, is not yet included in these treatment plan optimization processes. An operator's choice in photon energy is still limited to selecting one of the few discrete energy levels provided by the Linac. While some in the industry have used the word "energy modulation" with respect to radiation treatment, what is meant is making a choice among a few discrete energy levels available in the Linac, and not that the energy level is continuously varied.

Therefore, introducing the ability to continuously vary the energy level into the treatment planning process is desired.

SUMMARY

In one example, a method for photon energy synthesis is described. The method comprises obtaining, via a linear accelerator, a first photon energy beam dosimetric data, a second photon energy beam dosimetric data, and an intermediate photon energy beam dosimetric data, and fitting the first photon energy beam dosimetric data and the second photon energy beam dosimetric data linearly according to a preset fitting coefficient. The method further comprises generating a synthesized photon beam dosimetric data from the fitted first photon energy beam dosimetric data and the fitted second photon energy beam dosimetric data and calculating a dosimetric data fitting deviation based on a difference between the synthesized photon beam dosimetric data and an intermediate photon energy beam dosimetric data. The method then comprises comparing the fitting deviation with a preset threshold, wherein if the fitting deviation is less than or equal to the preset threshold, instructions are executed to apply the synthesized photon energy beam, and if the fitting deviation is greater than the preset threshold, instructions are executed to responsively adjust the preset fitting coefficient.

In another example, a radiation treatment system is provided. The system comprises a radiation source that directs an energy beam along a beam path toward a selected treatment target, an input device to receive a user-input photon energy beam value, a control unit to generate a synthesized photon energy beam matching the received photon energy beam value, wherein the synthesized photon energy beam comprises a value between two pre-set photon energy beam values provided on the radiation source, an energy modulation module in treatment plan optimization for 3D conformal radiation therapy (3DCRT), intensity modulated radiation therapy (IMRT), and volumetric modulated arc therapy (VMAT) plan optimization, and a communication module to convert and transfer the energy modulated treatment plan to the delivery system.

In another example, a radiation therapy device comprising a control unit having instructions stored in memory that are executed by a processor is provided. The functions provided by the device comprise decoding an energy modulated treatment plan comprising synthesized photon energies into radiation dose delivery instructions and delivering, via the radiation dose delivery instructions, photon energies either sequentially or simultaneously through fast energy switching to a subject. The sequential delivery can be performed by fast switching of the beam energy.

The features, functions, and advantages that have been discussed can be achieved independently in various examples or may be combined in yet other examples further details of which can be seen with reference to the following description and drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
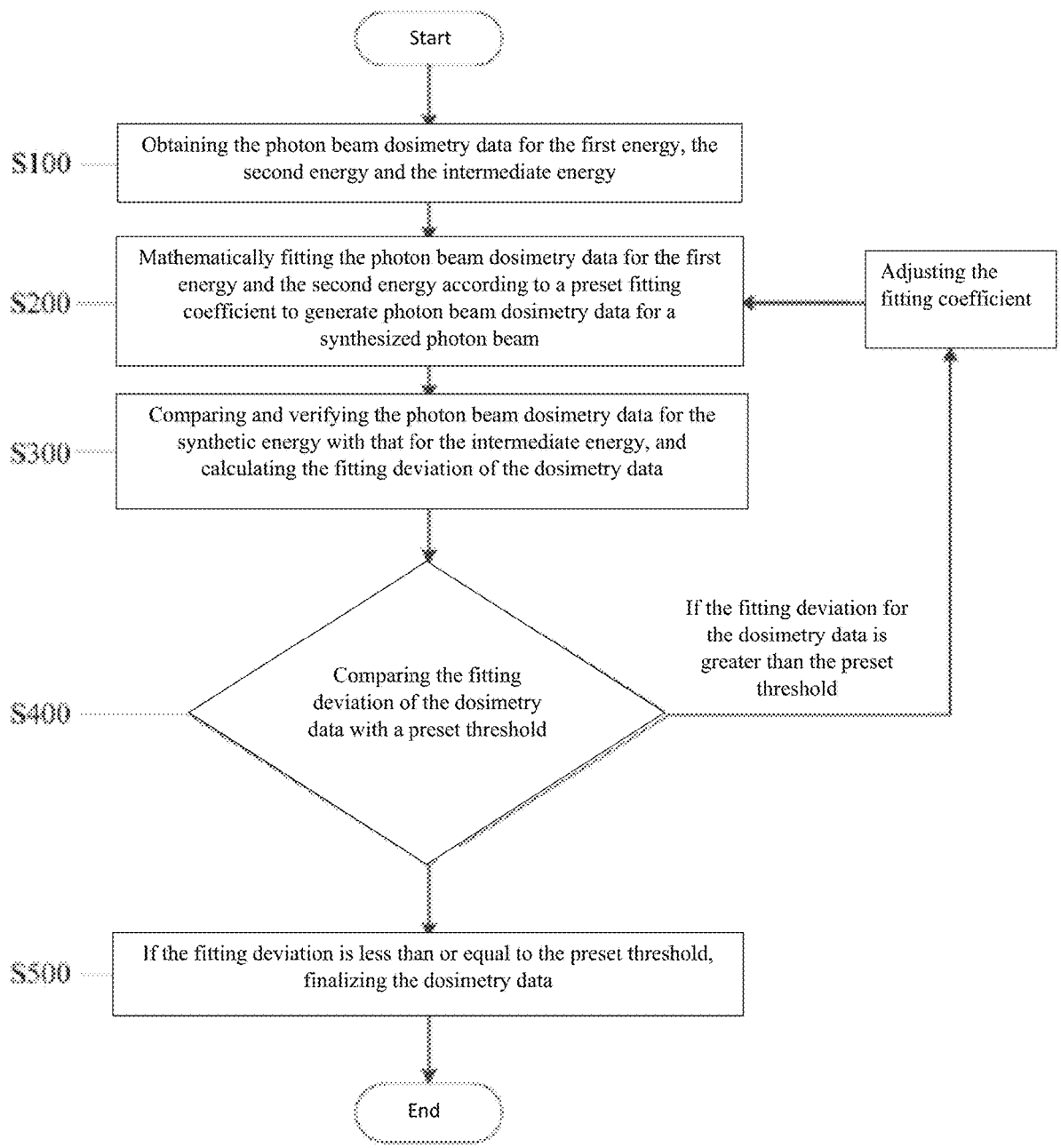
FIG. 1 depicts a simplified flow diagram of an example method that may be carried out to synthesize photon beams of known energies, in accordance with at least one embodiment.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

I. Overview

Examples, methods, and systems are described to generate a synthetic photon energy treatment plan. The systems and methods described herein provide for synthetic photon radiotherapy. Synthetic photon radiotherapy may take the form of photon beams of a known energy being synthesized from the combination of existing actual photon energies from a Linac, or any non-existent or continuous energy may be generated. Further, synthetic photon radiotherapy provides the capability of continuously varying photon energies.

The disclosed synthetic photon radiotherapy provides for matching any given known energy photon beam characteristics. Such matching can provide many clinical benefits. For example, a radiotherapy treatment plan of known photon energies can be delivered on the same or another Linac with different photon energies to achieve nearly identical dose distributions. Example scenarios that would call for a change in Linac are when one Linac requires repair but a patient treatment should not be cancelled, or when a patient is transferred to a new location to continue treatment on a different Linac.

As used herein, "subject" and "patient" are used interchangeably and refer to both human and nonhuman animals. The term "nonhuman animals" includes all vertebrates, e.g. mammals and non-mammals.

The terms "first," "second," and the like are only used for the purpose of description, and should not be understood as limiting or implying relative importance.

Recitation of ranges of values are merely intended to serve as a shorthand method of referring individually to each separate value falling within the range, unless otherwise indicated herein, and each separate value is incorporated into the disclosure as if it were individually recited herein. For example, if a concentration range is stated as 1% to 50%, it is intended that values such as 2% to 40%, 10% to 30%, or 1% to 3%, etc., are expressly enumerated in this disclosure. These are only examples of what is specifically intended, and all possible combinations of numerical values between and including the lowest value and the highest value enumerated are to be considered to be expressly stated in this disclosure.

Tumor depth is typically the primary factor in determining what photon energy level to use in a radiation treatment plan. Most radiation treatment plans consist of a plurality of photon beams that aim at a target from different directions. The tumor depth may vary among these different beams. For centrally located tumors, a single photon energy may be selected for the plan. If the tumor is not at the central region of the body, then different photon energies may be chosen. Traditionally, the photon energy was limited to the availability of a few discrete, photon energies pre-set on a Linac. However, the present disclosure provides for generation of a synthesized photon energy level, and thereby also for continuously variable photon energy, ranging between the lowest to the highest energy levels available on the Linac. In some embodiments, the synthesized photon energy can be used to guide optimization of a treatment plan.

While the terms "energy modulation" and "mixed energy photon therapy" have been used previously by others, such terms do not mean continuously variable photon energies, but rather a photon energy selection process from energy levels available on the Linac.

As used herein, the term "about" includes aspects of the recited characteristic, parameter, or value allowing for deviations or variations, including for example, tolerances, measurement error, measurement accuracy limitations and other factors known to skill in the art, and also ranges of the parameters extending a reasonable amount to provide for such variations.

FIG. 1 depicts a simplified flow diagram of an example method 100 that may be carried out to synthesize photon beams of known energies, in accordance with at least one embodiment.

Method 100 shown in FIG. 1 presents an example of a method that, for example, could be used with the system 200 shown in FIG. 2, for example. Method 100 includes one or more operations, functions, or actions as illustrated by one or more of steps S100-S500. Although the steps are illustrated in a sequential order, these steps may also be performed in parallel, and/or in a different order than those described herein. Also, the various steps may be combined into fewer steps, divided into additional steps, and/or removed based upon the desired implementation.

It should be understood that for this and other processes and methods disclosed herein, flowcharts show functionality and operation of one possible implementation of present examples. Alternative implementations are included within the scope of the examples of the present disclosure in which functions may be executed out of order from that shown or discussed, including substantially concurrent or in reverse order, depending on the functionality involved, as would be understood by those reasonably skilled in the art.

As shown at S100, a first photon energy beam dosimetric data, a second photon energy beam dosimetric data, and an intermediate photon energy beam dosimetric data are obtained. In some embodiments, a module such as a Linac may obtain such dosimetric data. In the present embodiment, the first photon energy beam has a lower energy value than the second photon energy beam, and the intermediate photon energy beam has an energy value in between the first photon energy and the second photon energy.

In some embodiments, some or all treatment plan parameters are required to be the same among the first photon energy beam and the second photon energy beam, such as the couch angle, gantry angle, collimator angle, beam modifier, multileaf collimator (MLC) aperture, and the like. However, in other embodiments, there may be no such requirement and the parameters may be different.

At S200, the photon beam dosimetric data is mathematically fitted for the first photon energy and the second photon energy according to a preset fitting coefficient, to generate photon beam dosimetric data for a synthesized photon energy.

In one example embodiment, the following formulae are used to obtain a synthesized photon energy:

$$PDD_{syn} = \alpha \cdot PDD_{low} + \beta \cdot PDD_{high} \qquad \text{Equation 1}$$

$$OAR_{syn} = \alpha \cdot OAR_{low} + \beta \cdot OAR_{high} \qquad \text{Equation 2}$$

wherein $PDD_{syn}$ indicates the PDD of a synthesized photon energy beam, $PDD_{low}$ represents the first photon energy beam, $PDD_{high}$ represents the second photon energy beam, and $\alpha$ and $\beta$ represent fitting coefficients. OAR represents a dose profile, or Off Axis Ratio. For any of the embodiments discussed herein, it is preferable that the dosimetric data comprises PDD and OAR data. Dosimetric data representing a photon energy may have a different format, for example, a dose matrix in the 3-dimensional space, which can be reduced to many simplified form such as PDD and OAR.

At S300, a fitting deviation is calculated between the synthetic photon beam dosimetric data and the intermediate photon energy beam dosimetric data. The following is applied:

$$R^j = W_{PDD} \cdot \frac{1}{N} \sum_{i=1}^{N} |PDD_{Syn} - PDD_{Mid}| + \qquad \text{Equation 3}$$

$$W_{OAR} \cdot \frac{1}{M} \sum_{i=1}^{M} |OAR_{Syn} - OAR_{Mid}|$$

wherein Mid indicates the energy value for the intermediate energy photon beam dosimetric data, and $R^j$ indicates the fitting deviation or residual difference at the jth step of the synthesis photon energy beam dosimetric data and the intermediate energy photon beam dosimetric data. $W_{PDD}$ and $W_{OAR}$ are the weighting of the PDD and OAR. N and M are the number of data points in PDDs and OARs. The goal with Equation 5 is to minimize R. Other forms of R can also be used, for example, the absolute operator "||" can be replaced with a square, to achieve the same goal.

At S400, the fitting deviation of the dosimetric data, $R^j$, is compared with a preset threshold, δ, to obtain a comparison result. If the fitting deviation for the dosimetric data is greater than the preset threshold, the fitting coefficient is responsively adjusted, with the method returning to execute steps S200-S400, until the fitting deviation of the revised synthesis photon energy beam is less than or equal to the preset threshold.

Thus, in accordance with step S400, for example, if $R^j \leq \delta$, wherein δ indicates a preset threshold value, the dosimetric data fitness bias is less than the preset threshold, and if $Rj > \delta$, the dosimetric data fitness bias is greater than the preset threshold.

At S500, if the dosimetric data fitting deviation is less than or equal to the preset threshold, then synthesis of the photon energy beam dosimetric data is considered success and the fitting process completes.

The method S100-S500 is applicable to photon energies with and/or without internal flattening filters and beam modifiers, such as wedges.

Thus, the synthesized photo beam comprises an energy at some level within the range between the first photon beam energy and the second photon beam energy. The system described above is cost efficient for a Linac, as fewer photon beam values need to be implemented onto the machine. A further benefit is providing a maximum degree of freedom for operation of a Linac, by generating the capability of continuous variation of photon beam energy within a given range. For example, a radiotherapy treatment plan comprising a plurality of photon beams at various energy levels can be delivered on a Linac comprising only two photon energies to achieve near identical dose distributions. The resulting synthetic photon beam generated via steps S100-S500 comprises an energy varying continuously from the lowest to the highest available actual photon beams from the one or more Linacs used, and thus is not limited to any pre-existing photon energies.

Both forward and inverse planning modes can be deployed to achieve the photon beam energy modulation described herein. The term "forward planning" refers to an operator manually choosing any photon energy for a plan or for each beam based on past experience and knowledge, before further plan optimization is performed, such as 3D conformal radiotherapy (3DCRT), IMRT, or VMAT. The operator has the option to manually vary the energy again afterwards during plan evaluation. Internally, the module decodes the chosen photon energy based on the synthesis of existing low and high photon energies. The term "inverse planning" refers to determining an effective energy automatically based on given prescriptions and constraints; that is, as part of or as a result of the plan optimization. The effective energy can be for each plan, each beam, each sub-field, each beamlet, or at each gantry angle. This can have a significant effect as the energy parameter may be dropped from the physician prescription written directive.

Figure 2A:
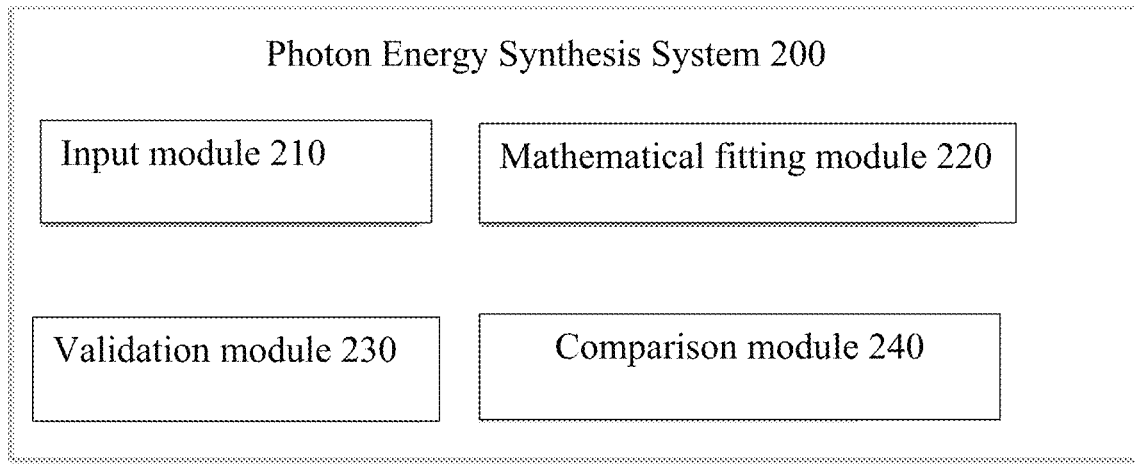
FIG. 2a depicts a simplified block diagram of a photon energy synthesis system, in accordance with at least one embodiment.

FIG. 2a depicts a simplified block diagram of a photon energy synthesis system 200, in accordance with at least one embodiment. The system 200 comprises an input module 210 such as a Linac, for obtaining photon energy beam dosimetric data. For example, the input module 210 may obtain a first photon energy beam dosimetric data, a second photon energy beam dosimetric data, and an optional intermediate photon energy beam dosimetric data, as described with reference to FIG. 1. In the absence of the intermediate photon beam dosimetric data, the coefficients α and β can be continuously varied, to synthesize a new photon energy, as described herein.

The system 200 further comprises a mathematical fitting module 220, a validation module 230, and a comparison module 240. The mathematical fitting module 220, the validation module 230, and the comparison module 240 may each separately or collectively comprise a control unit or may be operatively coupled to a control unit configured to execute a set of instructions that are stored in one or more storage elements, or memory, in order to process data. As used herein, the term "control unit" may include any processor-based or microprocessor-based system including systems using microcontrollers, logic circuits, and any other circuit or processor including hardware, software, or a combination thereof capable of executing the functions described herein. The memory may be in the form of an information source or a physical memory element. The set of instructions may include various commands that instruct the modules 220, 230, 240 to perform specific operations such as the methods and processes of the various examples of the subject matter described herein. The set of instructions may be in the form of a software program. Software may be stored on a tangible and non-transitory computer readable storage medium, such as a computer hard drive, ROM, RAM, or the like. The instructions, for example, may comprise instructions to execute steps S200-S500 described with reference to FIG. 1. In some embodiments, a remote control system may communicate with the modules and/or the control unit of the system 200.

The mathematical fitting module 220 may generate synthesized photon beam dosimetric data from two or more photon beam dosimetric data. For example, the mathematical fitting module 220 may comprise instructions to execute step S200 described with reference to FIG. 1.

The validation module 230 may compare the synthesized photon beam dosimetric data with an intermediate photon energy beam dosimetric data, and calculate a fitting deviation between the synthesized photon beam dosimetric data and the intermediate photon energy beam dosimetric data. The validation module 230 may comprise instructions to execute step S300 described with reference to FIG. 1.

The comparison module 240 may compare the fitting deviation with a preset threshold. The comparison module 240 may comprise instructions to execute steps S400-S500 described with reference to FIG. 1. If the fitting deviation is less than or equal to the preset threshold, the comparison module 240 may execute instructions to finalize the dosimetric data to be the final dose data. If, however, the fitting deviation is greater than the preset threshold, the comparison module 240 may execute instructions to responsively adjust the preset fitting coefficient. Adjusting the fitting coefficient may comprise further optimizing and revising the coefficient value.

Figure 2B:
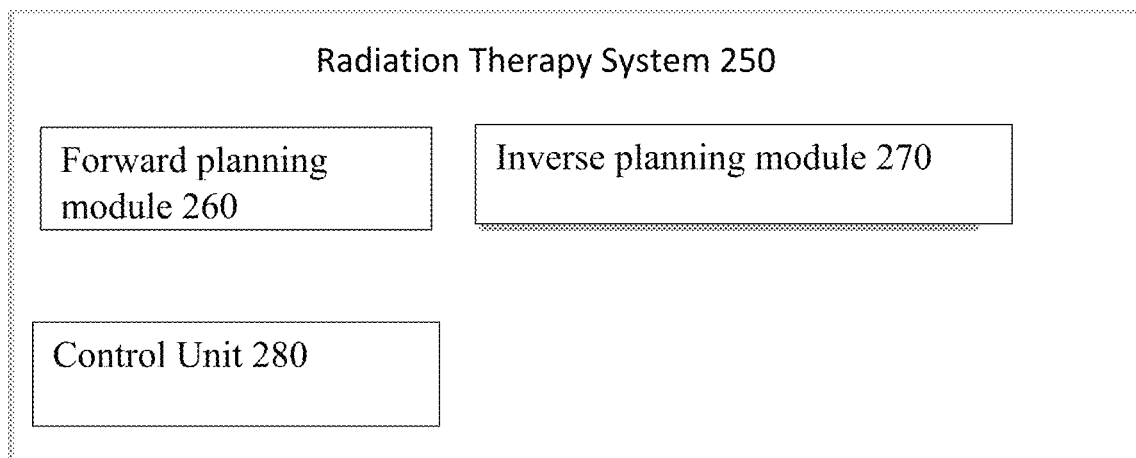
FIG. 2b depicts a simplified block diagram of a radiation therapy system, in accordance with at least one embodiment.

FIG. 2b depicts a simplified block diagram of a radiation therapy system 250, in accordance with at least one embodiment. The system 250 comprises a forward planning module 260 such as 3DCRT, IMRT, or VMAT, an inverse planning module 270 such as 3DCRT, IMRT, or VMAT, and a communication module 270, to convert or transfer a treatment plan from TPS to a delivery system, for example a Linac. The forward planning module 260 and the inverse planning module 270 may comprise energy modulation as part of the treatment plan optimization. A control unit 280 may generate a synthesized photon energy beam as discussed herein.

It is critical to deliver appropriate doses of radiation that will have the intended effect on a patient as radiation therapy is not reversible. That is, once given to a patient, radiation doses cannot be extracted and re-delivered. Thus, having an effective radiation therapy system to define the treatment parameters and action sequence for execution by a Linac, is important.

II. Examples

An evaluation was performed to investigate generation of and application of a synthetic photon energy beam for use in a treatment plan. In the study, a Varian Truebeam® Linac at a field size of 10×10 cm$^2$ obtained PDDs at 6 MV, 10 MV, and 15 MV. A PDD for a synthetic 10 MV was synthesized from the 6 MV and the 15 MV photon energy beams, and a least square fit was performed. The synthetic 10 MV was further validated in a 5-field 10 MV prostate tumor treatment plan. The study discussed below illustrates how a Linac with two photon energies is capable, using the methods and systems described herein, of producing dosimetrically equivalent plans of any energy between the two given photon energies.

Figure 3:
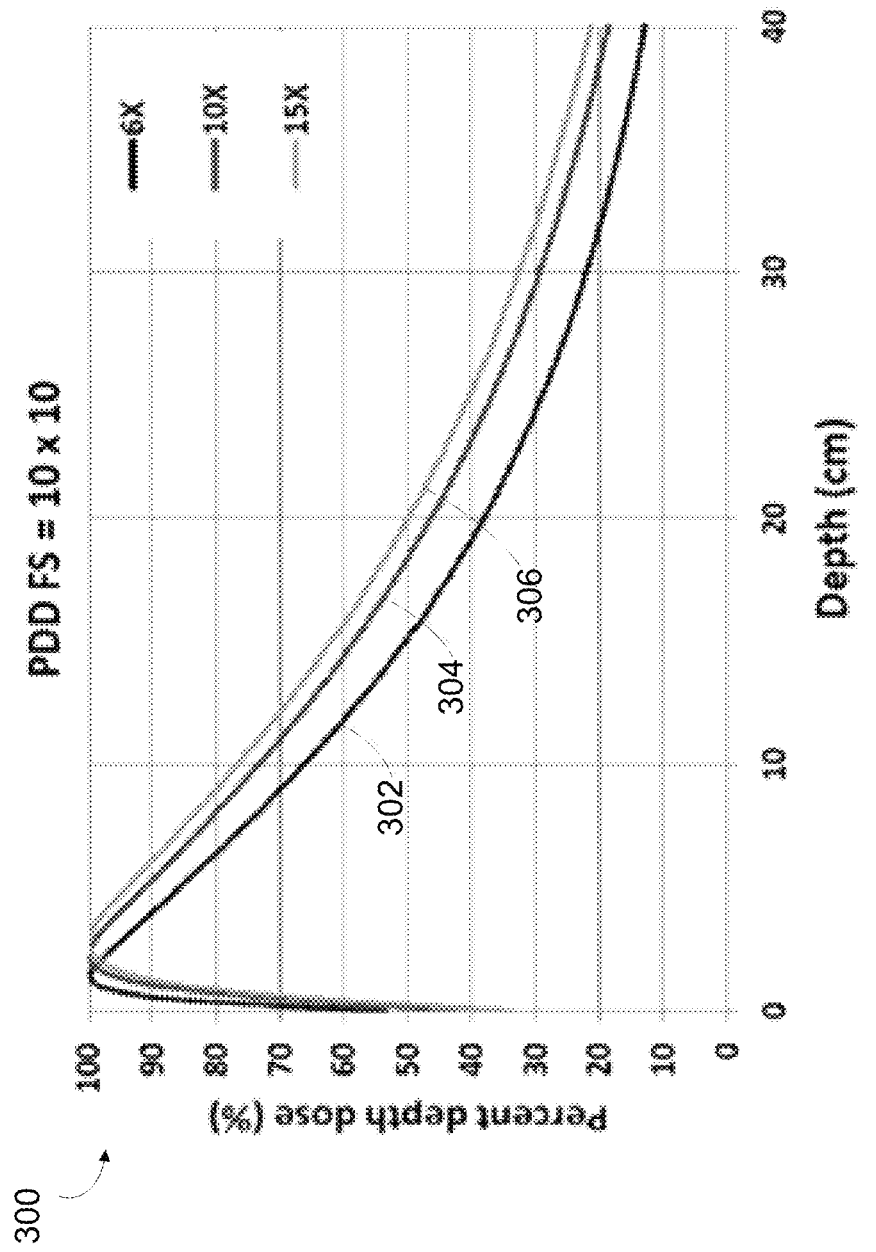
FIG. 3 depicts a graph illustrating PDD plotted over depth along the axis of the radiation beam, in accordance with at least one embodiment.

FIG. 3 depicts a graph 300 illustrating PDD plotted over depth along the axis of the radiation beam, in accordance with at least one embodiment. Photon beams are commonly characterized by the PDD in water phantom at a fixed source to surface distance (SDD) for a range of field sizes and profiles. As discussed above, a field size of 10×10 cm$^2$ was used. Three curves are plotted in graph 300: a curve 302 for a photon beam of 6 MV (corresponding to low energy), a curve 304 for a photon beam of 10 MV (corresponding to intermediate energy), and a curve 306 for a photon beam of 15 MV (corresponding to high energy).

Figure 4:
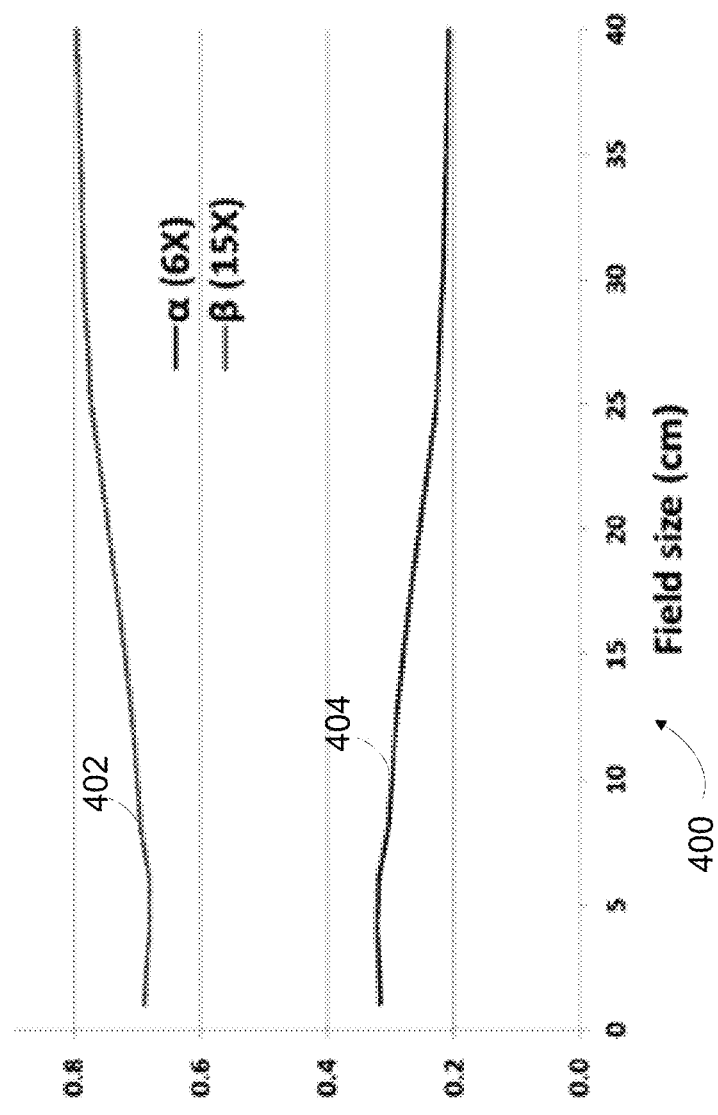
FIG. 4 depicts a graph plotting α and β over field size, in accordance with at least one embodiment.

FIG. 4 depicts a graph 400 plotting α 404 and β 402 over field size, in accordance with at least one embodiment. In FIG. 4, α and β comprise fitting coefficients such as described with reference to FIGS. 1 and 2, wherein α is applied to the photon beam of 6 MV and β to the photon beam of 15 MV.

Figure 5:
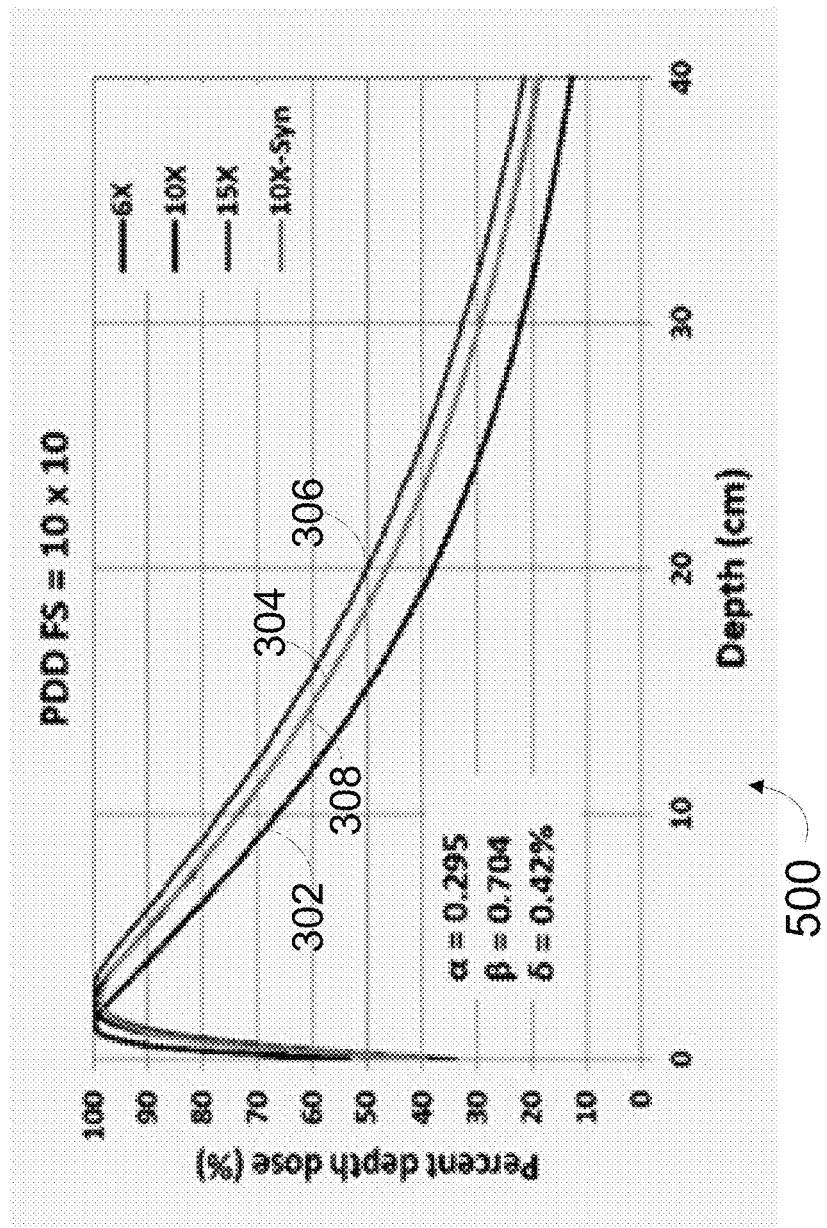
FIG. 5 depicts a graph illustrating PDD plotted over depth along the axis of the radiation beam, with synthesis dosimetric data added, in accordance with at least one embodiment.

FIG. 5 depicts a graph 500 illustrating PDD plotted over depth along the axis of the radiation beam, with synthesis dosimetric data 308 added, 10 MV-Syn, in accordance with at least one embodiment. As can be seen in FIG. 5, the synthesis dosimetric data 308 covers most of the intermediate dosimetric data 304, illustrating a successful generation of a 10 MV photon beam.

Figure 6:
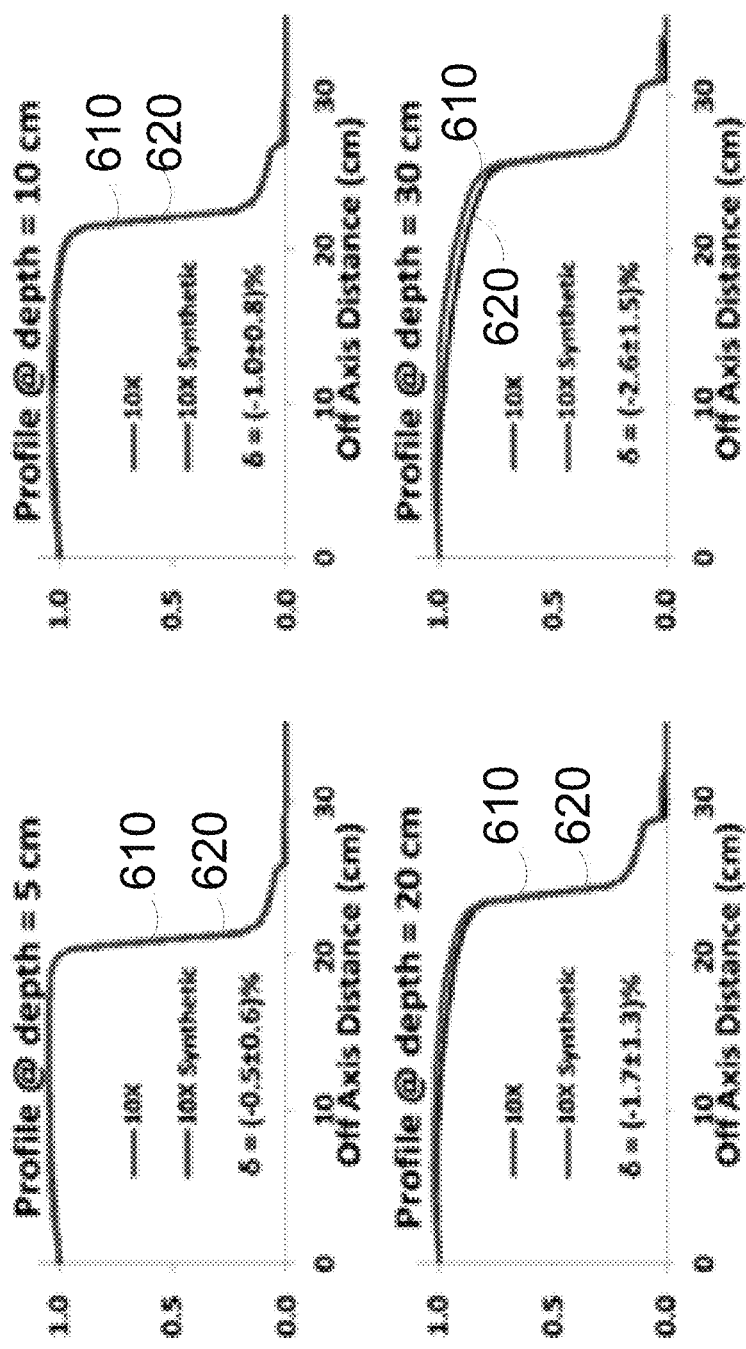
FIG. 6 depicts a series of graphs comparing profiles of the synthetic dosimetric data with the intermediate dosimetric data at varying depths, in accordance with at least one embodiment.

FIG. 6 depicts a series of graphs 600 comparing profiles of the synthetic dosimetric data 610 with the intermediate dosimetric data 620 at varying depths, in accordance with at least one embodiment. The intermediate dosimetric data 620 represents data obtained at 10 MV from a Linac.

Figure 7:
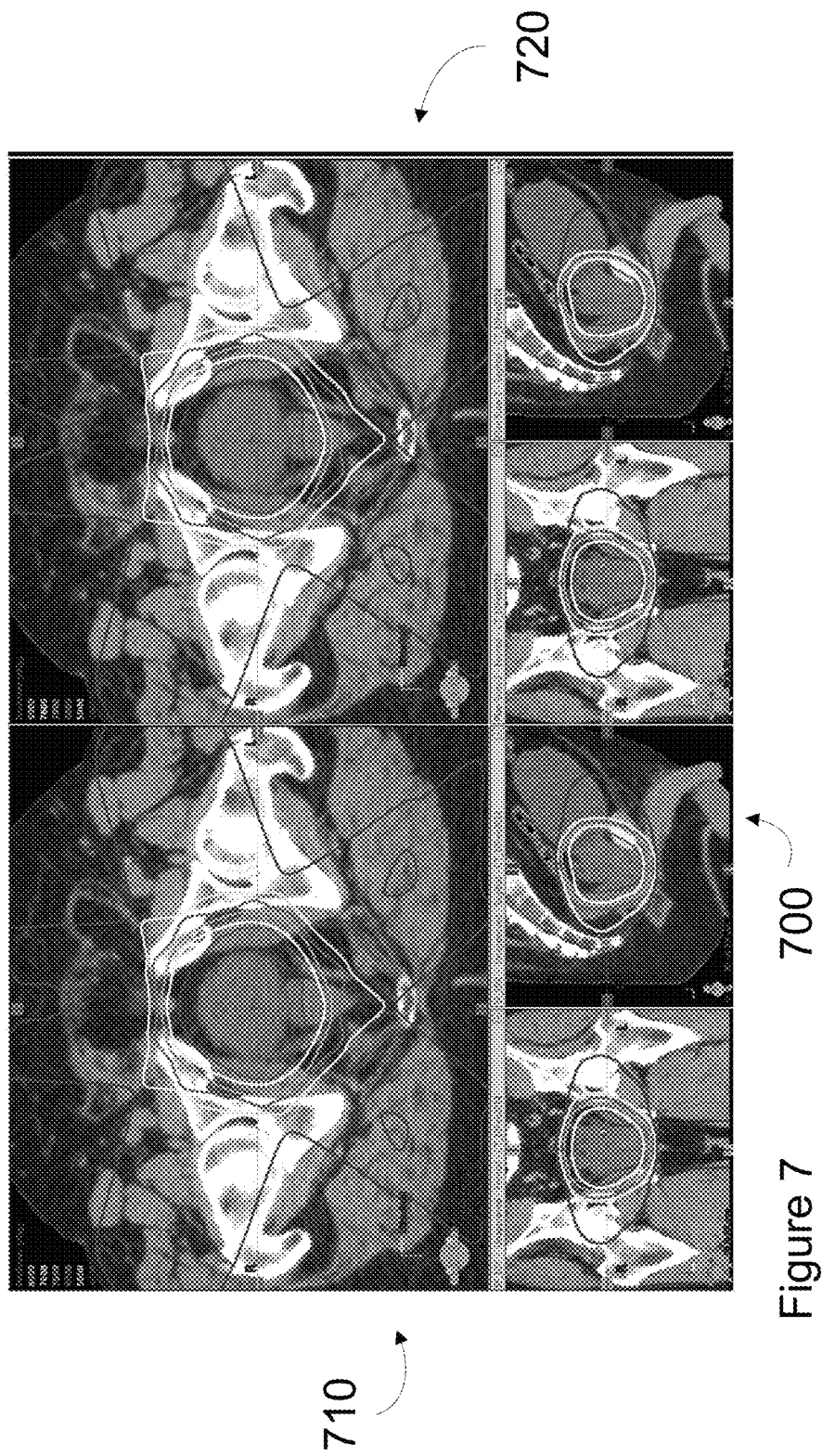
FIG. 7 depicts images on a display of an example planning system, in accordance with at least one embodiment.

FIG. 7 depicts images 700 on a display of an example treatment planning system, in accordance with at least one embodiment. The images 700 are obtained from a 5-field 10 MV 3DCRT prostate cancer treatment plan. A first series of images 710 (left) show the target (in red shaded region) and the associated radiation dose distribution (series of concentric solid lines representing different dose levels) for an actual 10 MV photon energy on the Linac. A second series of images 720 (right) show the same region and associated dose distributions from the synthetically derived 10 MV plan. The almost identical concentric isodose lines in 710 and 720 demonstrate the very similar dose distributions (i.e., the radiation outcome) from these two treatment plans.

Figure 8:
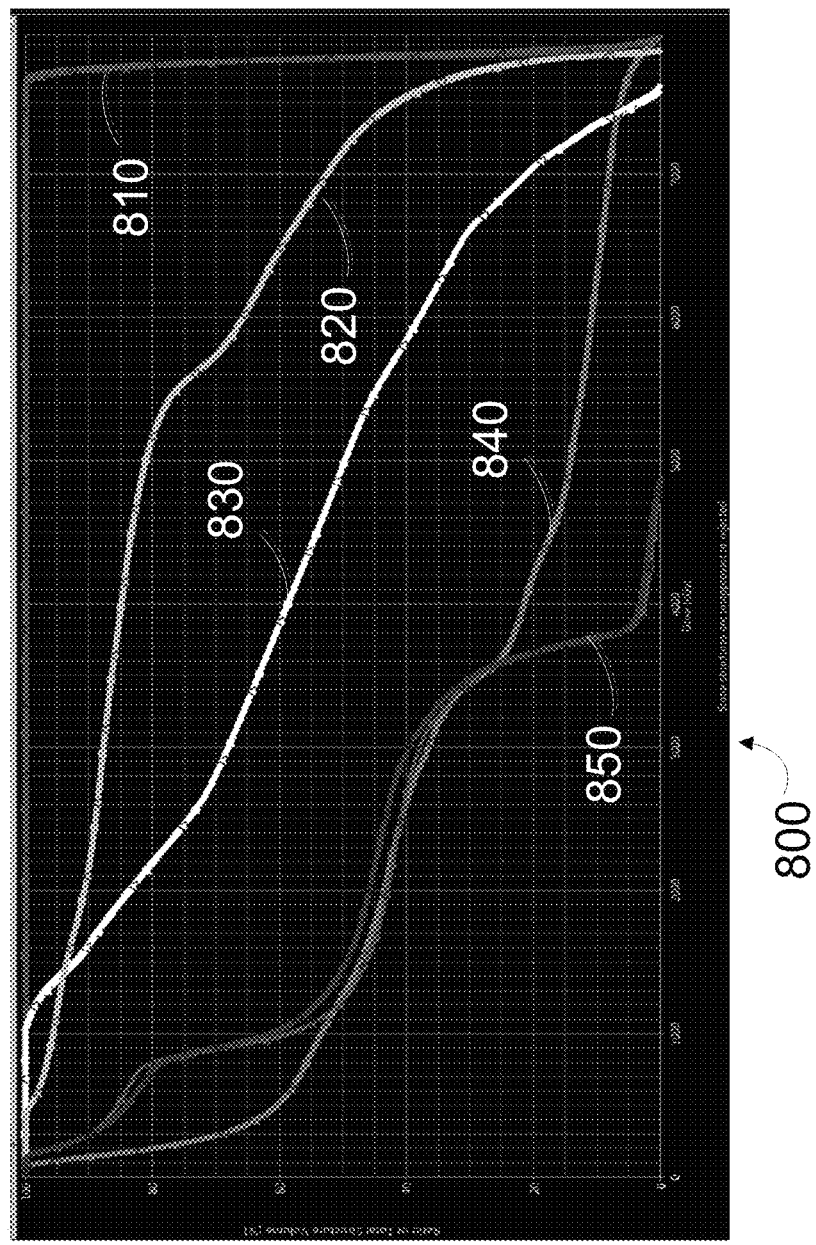
FIG. 8 depicts a graph in a display of the example planning system of FIG. 7, in accordance with at least one embodiment.

FIG. 8 depicts a graph 800 in a display of the example treatment planning system of FIG. 7, in accordance with at least one embodiment. In graph 800, each line, also called a dose volume histogram, represents a structure of interest, with line 810 representing PTV (prostate target), line 820 representing the rectum, line 830 representing the penile bulb, line 840 representing the bladder, and line 850 representing the femoral heads. Each line has two types of markers (squares and triangles) embedded, representing the two plans depicted in FIG. 7. These lines are commonly used to evaluate the treatment plans. The fact that each line is actually the superposition of two lines from the two plans supports the notion that these two plans are almost identical: the original 10 MV plan and the synthetic 10 MV plan.

Figure 9:
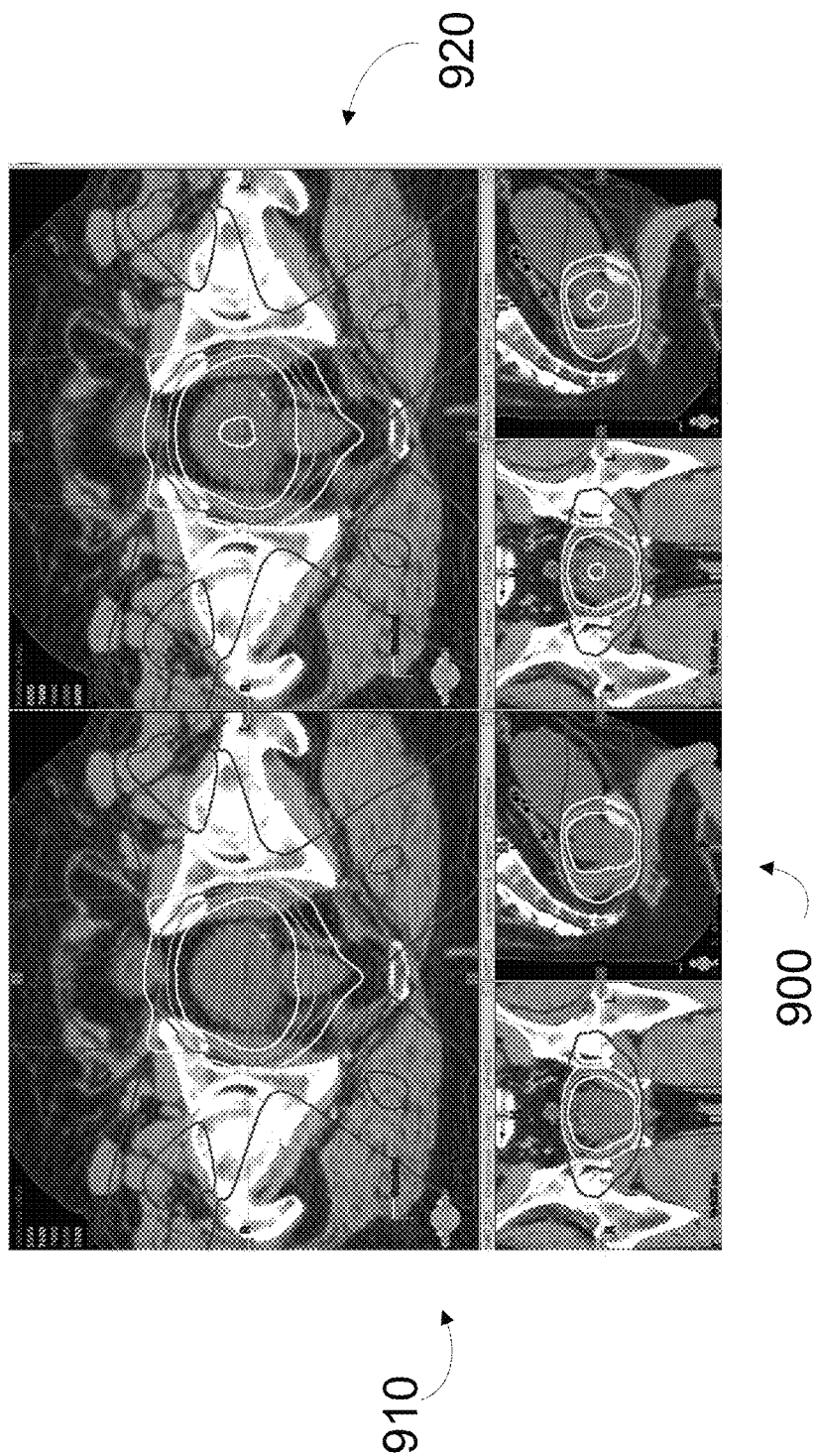
FIG. 9 depicts images on a display of an example planning system, in accordance with at least one embodiment.

FIG. 9 depicts images 900 on a display of an example treatment planning system, in accordance with at least one embodiment. The images 900 are obtained from a 5-field 10 MV IMRT prostate tumor treatment plan. A first series of images 910 (left) show the target (in red shaded region) and the associated radiation dose distribution (series of concentric solid lines representing different dose levels) for an actual 10 MV photon energy on the Linac. A second series of images 920 (right) show the same region and associated dose distributions from the synthetically derived 10 MV plan. The almost identical concentric isodose lines in 910 and 920 demonstrate the very similar dose distributions (i.e., the radiation outcome) from these two treatment plans.

Figure 10:
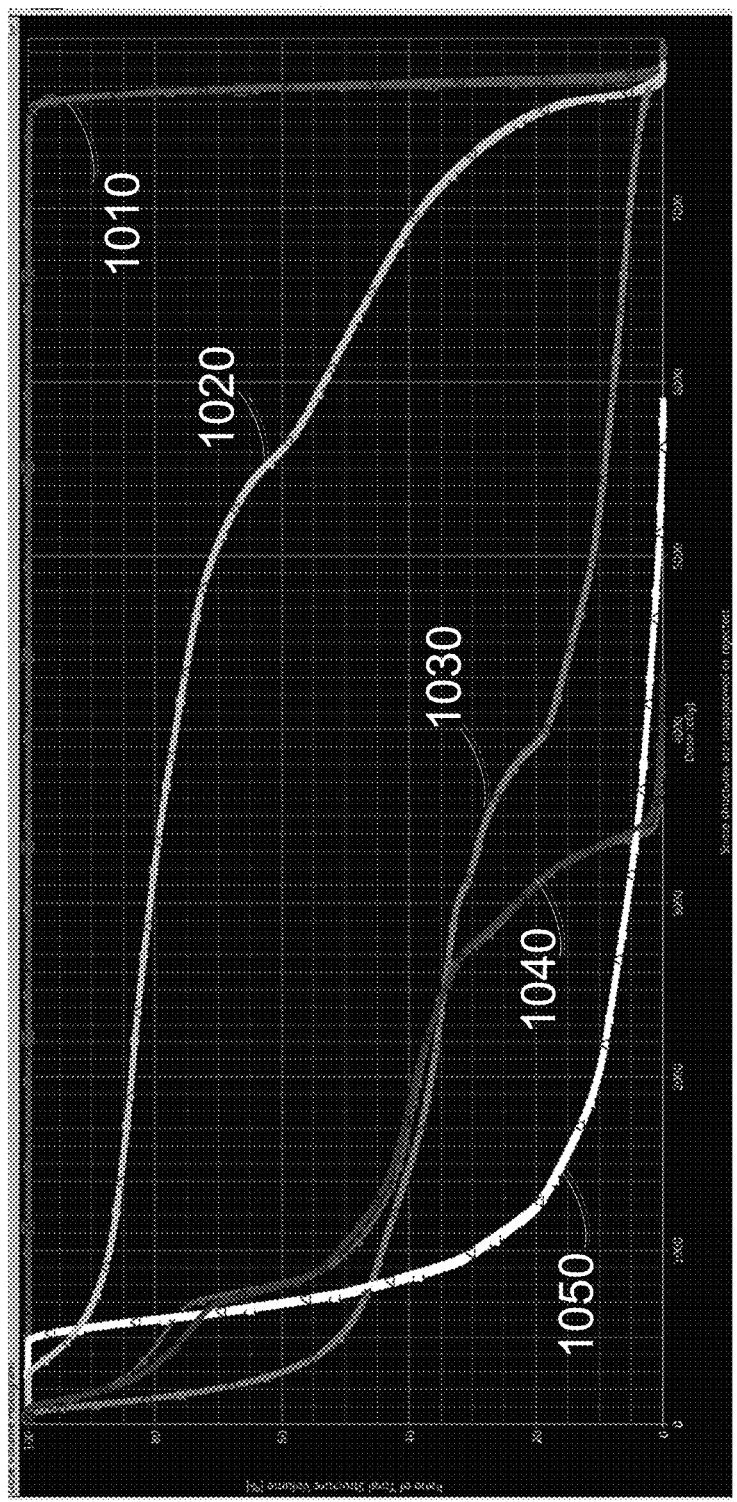
FIG. 10 depicts a graph in a display of the example planning system of FIG. 9, in accordance with at least one embodiment.

FIG. 10 depicts a graph 1000 in a display of the example planning system of FIG. 9, in accordance with at least one embodiment. In graph 1000, line 1010 represents PTV, line 1020 represents the rectum, line 1040 represents the penile bulb, line 1030 represents the bladder, and line 1050 represents the femoral heads. As the graph 1000 shows, each line comprises the superposition of two lines from the two plans, supporting the notion that these two plans are almost identical: the original 10 MV plan and the synthetic 10 MV plan. Notably, IMRT is a more advanced technology that incorporates more complex software, rendering synthesis more difficult, and yet as the images 910 and 920 show, as well as the graph 1000, successful outcomes using the synthetic 10 MV are achieved. One advantage of the IMRT plan in this Figure over the 3DCRT plan in FIGS. 7 and 8 is that the concentric dose levels are tighter, meaning the radiation dose is more conformal and delivers less dose to the surrounding critical organs. For example, the penile bulb received a significantly lower dose in IMRT plan than in the 3DCRT plan.

Figure 11:
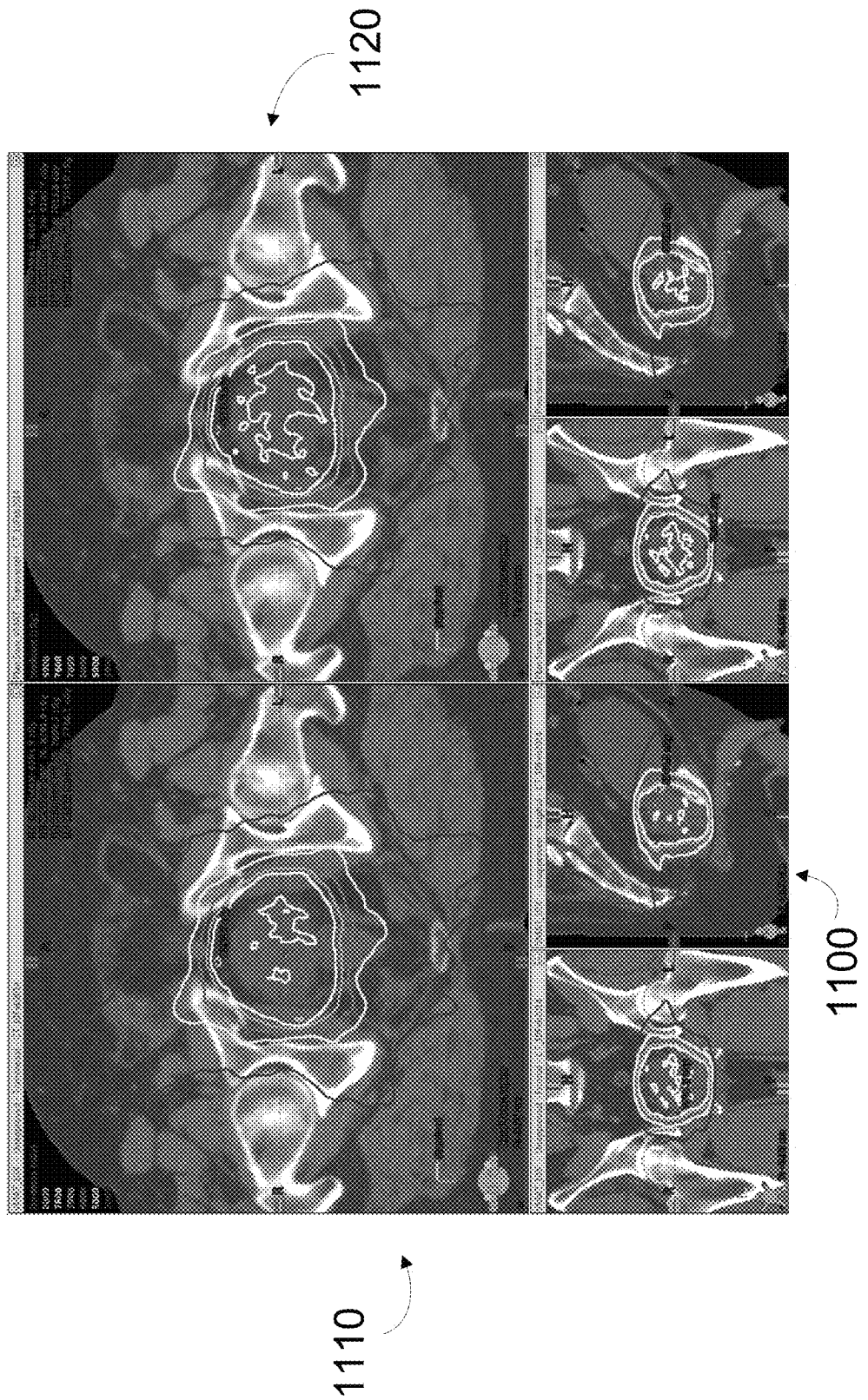
FIG. 11 depicts images on a display of an example planning system, in accordance with at least one embodiment.

FIG. 11 depicts images 1100 on a display of an example planning system, in accordance with at least one embodiment. The images 1100 are obtained from a 2-arcs 10 MV VMAT prostate tumor treatment plan. A first series of images 1110 (left) show the target (in red shaded region) and the associated radiation dose distribution (series of concentric solid lines representing different dose levels) for an actual 10 MV photon energy on the Linac. A second series of images 1120 (right) show the same region and associated dose distributions from the synthetically derived 10 MV plan. The almost identical concentric isodose lines in 1110 and 1120 demonstrate the very similar dose distributions (i.e., the radiation outcome) from these two treatment plans.

Figure 12:
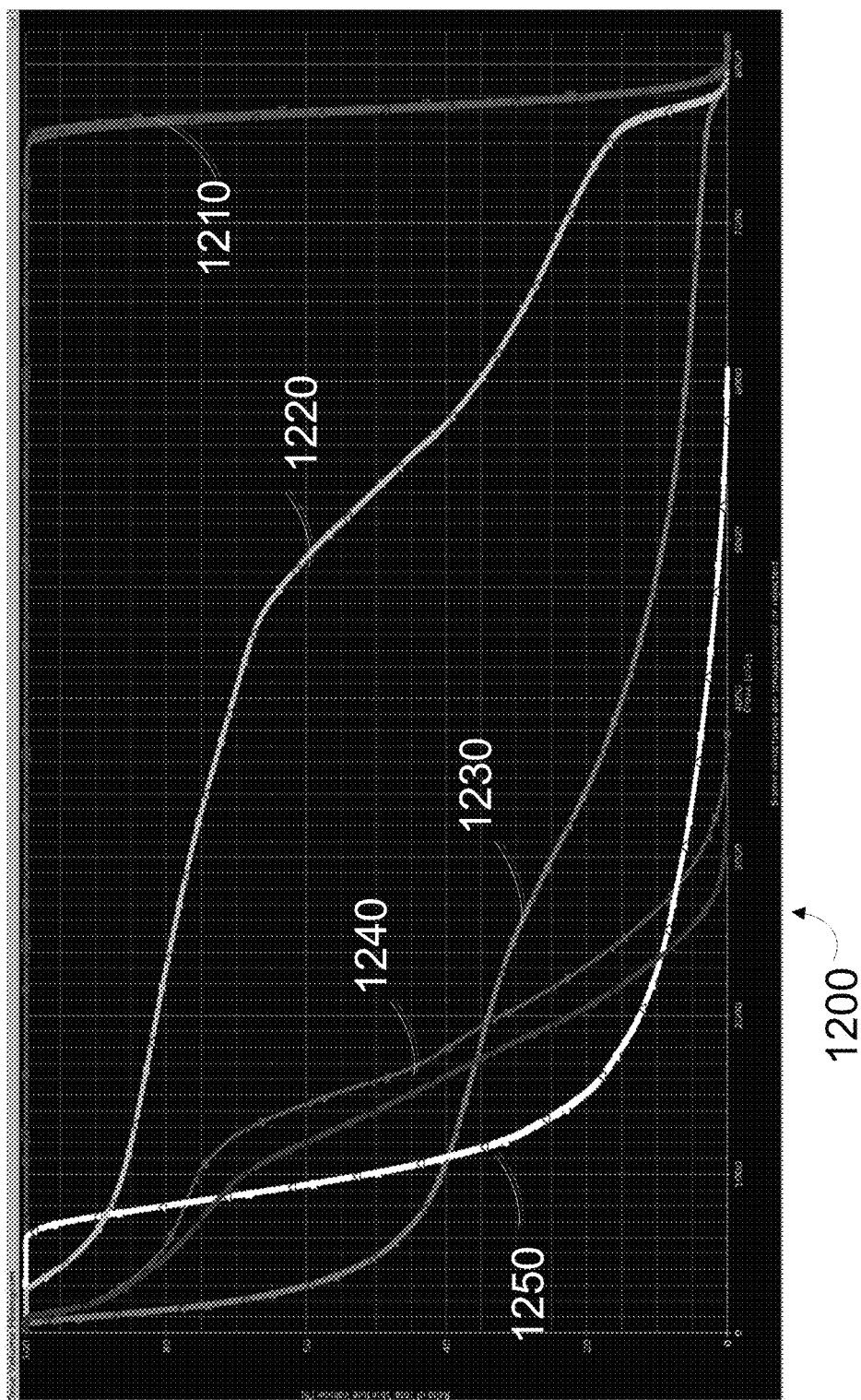
FIG. 12 depicts a graph in a display of the example planning system of FIG. 11, in accordance with at least one embodiment.

FIG. 12 depicts a graph 1200 in a display of the example planning system of FIG. 11, in accordance with at least one embodiment. In graph 1200, line 1210 represents PTV, line 1220 represents the rectum, line 1250 represents the penile bulb, line 1230 represents the bladder, and line 1240 represents the femoral heads. As the graph 1200 shows, each line comprises the superposition of two lines from the two plans, supporting the notion that these two plans are almost identical: the original 10 MV plan and the synthetic 10 MV plan. Similarly as with IMRT, VMAT is a more recent, advanced technology that incorporates more complex software, rendering synthesis more difficult, and yet as the images 1110 and 1120 show, as well as the graph 1200, successful outcomes using the synthetic 10 MV are achieved.

Thus, as described with reference to FIGS. 3-12, it is possible to construct a synthetic 10 MV photon beam using only 6 MV and 15 MV photon beams. As shown in the example above, the coefficients vary with field size. The root mean square error (RMSE) is less than 0.5%, which is comparable or better than the specifications of energy matches provided by Linac vendors.

FIGS. 3-12 demonstrate methods and systems for producing a given photon energy between two existing photon energies on a Linac. Advantageously, it is unnecessary to have more than two photon energies on a Linac. Furthermore, the example described above also provides a mechanism to treat a patient of an existing plan with an equivalent plan by using neighboring photon energies if the actual photon energy called for in a plan is unavailable or not offered on a given Linac.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. A photon energy synthesis method comprising:
obtaining, via a linear accelerator, a first photon energy beam dosimetric data, a second photon energy beam dosimetric data, and an intermediate photon energy beam dosimetric data;
fitting the first photon energy beam dosimetric data and the second photon energy beam dosimetric data according to a preset fitting coefficient;
generating a synthesized photon beam dosimetric data from the fitted first photon energy beam dosimetric data and the fitted second photon energy beam dosimetric data;
calculating a dosimetric data fitting deviation based on a difference between the synthesized photon beam dosimetric data and the intermediate photon energy beam dosimetric data, and responsively:
comparing the fitting deviation with a preset threshold;
if the fitting deviation is less than or equal to the preset threshold, executing instructions to apply the synthesized photon energy beam; and
if the fitting deviation is greater than the preset threshold, executing instructions to responsively adjust the preset fitting coefficient,
wherein at least one of the first energy photon beam dosimetric data, the second energy photon beam dosimetric data, and the intermediate energy photon beam dosimetric data are obtained from a second linear accelerator.

2. The method of claim 1, wherein the dosimetric data comprises percent depth-dose curves and an off-axis dose profile.

3. The method of claim 1, wherein generating the synthesized photon beam dosimetric data further comprises adding the fitted first photon energy beam dosimetric data and the fitted second photon energy beam dosimetric data.

4. The method of claim 3, wherein the fitting comprises linear fitting, and wherein the fitted first photon energy beam dosimetric data comprises a first fitting coefficient and the fitted second photon energy beam dosimetric data comprises a second fitting coefficient.

5. The method of claim 1, wherein executing instructions to apply the synthesized photon energy beam further comprises executing instructions to submit the synthesized photon energy into a treatment planning module comprising at least one of 3DCRT, IMRT, and VMAT.

6. The method of claim 1, wherein executing instructions to apply the synthesized photon energy beam further comprises executing instructions to deliver a photon energy beam comprising the synthesized photon beam dosimetric data along a beam path toward an object in a subject.

7. The method of claim 6, wherein the object is a tumor.

8. A photon energy synthesis method comprising:
obtaining, via a linear accelerator, a first photon energy beam dosimetric data, a second photon energy beam dosimetric data, and an intermediate photon energy beam dosimetric data;
fitting the first photon energy beam dosimetric data and the second photon energy beam dosimetric data according to a preset fitting coefficient;
generating a synthesized photon beam dosimetric data from the fitted first photon energy beam dosimetric data and the fitted second photon energy beam dosimetric data;
calculating a dosimetric data fitting deviation based on a difference between the synthesized photon beam dosimetric data and the intermediate photon energy beam dosimetric data, and responsively:
comparing the fitting deviation with a preset threshold;
if the fitting deviation is less than or equal to the preset threshold, executing instructions to apply the synthesized photon energy beam comprising executing instructions to submit the synthesized photon energy into a treatment planning module comprising at least one of 3DCRT, IMRT, and VMAT; and
if the fitting deviation is greater than the preset threshold, executing instructions to responsively adjust the preset fitting coefficient.

9. The method of claim 8, wherein the first energy photon beam dosimetric data, the second energy photon beam dosimetric data, and the intermediate energy photon beam dosimetric data are obtained on the same linear accelerator.

10. The method of claim 8, wherein the dosimetric data comprises percent depth-dose curves and an off-axis dose profile.

11. The method of claim 8, wherein generating the synthesized photon beam dosimetric data further comprises adding the fitted first photon energy beam dosimetric data and the fitted second photon energy beam dosimetric data.

12. The method of claim 11, wherein the fitting comprises linear fitting, and wherein the fitted first photon energy beam dosimetric data comprises a first fitting coefficient and the fitted second photon energy beam dosimetric data comprises a second fitting coefficient.

13. The method of claim 8, wherein executing instructions to apply the synthesized photon energy beam further comprises executing instructions to deliver a photon energy beam comprising the synthesized photon beam dosimetric data along a beam path toward an object in a subject.

14. The method of claim 13, wherein the object is a tumor.

* * * * *